United States Patent [19]
Novello

[11] 3,988,324
[45] Oct. 26, 1976

[54] 3-DIAZINE SUBSTITUTED BENZOTHIADIAZINES

[75] Inventor: Frederick C. Novello, Berwyn, Pa.

[73] Assignee: Merck & Co., Inc., Rahway, N.J.

[22] Filed: Aug. 29, 1975

[21] Appl. No.: 609,111

Related U.S. Application Data

[62] Division of Ser. No. 509,975, Sept. 26, 1974, which is a division of Ser. No. 236,243, March 20, 1972, Pat. No. 3,890,313.

[52] U.S. Cl. ............................ 260/243 D; 424/246
[51] Int. Cl.² ............... C07D 285/20; C07D 285/22
[58] Field of Search ................................. 260/243 C

[56] References Cited
UNITED STATES PATENTS 3,890,313   6/1975   Novello ........................ 260/243 C

*Primary Examiner*—Nicholas S. Rizzo
*Attorney, Agent, or Firm*—Daniel T. Szura; J. Jerome Behan

[57] ABSTRACT

3-Diazine(or substituted diazine)-1,2,4-benzothiadiazine-1,1-dioxide products or 3,4-dihydro derivatives thereof are described. Products are prepared by conventional methods employing the appropriate sulfamoylaniline and diazine carboxylic acid halide or diazine carboxaldehyde. Products are xanthine oxidase inhibitors.

7 Claims, No Drawings

3-DIAZINE SUBSTITUTED BENZOTHIADIZINES

This is a division of co-pending U.S. application Ser. No. 509,975 filed Sept. 26, 1974, which in turn is a division of U.S. application Ser. No. 236,243, filed Mar. 20, 1972 now U.S. Pat. No. 3,890,313.

This invention is concerned with benzothiadiazine compounds having a 3-diazine substituent which have been found to exhibit marked xanthine oxidase inhibiting properties equal to or greater than exhibited by allopurinol when all compounds are evaluated in the same in vitro test.

The novel products of this invention have the structural formula

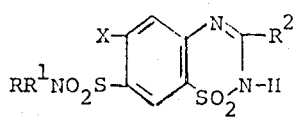

I

OR

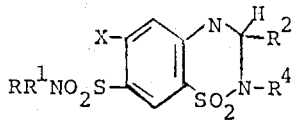

II and pharmacologically acceptable salts thereof wherein R, $R^1$ and $R^4$ are similar or dissimilar groups selected from hydrogen and lower alkyl having from 1 to 5 carbon atoms, X is selected from halogen, particularly chloro or bromo, trifluoromethyl, and lower alkyl having advantageously from 1 to 3 carbon atoms and $R^2$ is a diazine attached through one of its carbon atoms to the benzothiadiazine nucleus and optionally mono- or di-substituted with similar or dissimilar groups selected from $C_{1-3}$ alkyl, halo, advantageously chloro and bromo, and hydroxy. The diazine substituent is derived from a pyrazine, pyridazine or pyrimidine and attachment to the benzothiadiazine nucleus can be through any of the available carbons of the diazine nucleus.

The products of this invention can be prepared by one or another of the well known procedures for making benzothiadiazine compounds of structure I or 3,4-dihydrobenzothiadiazine compounds of structure II.

In general, the benzothiadiazine compounds of structure I can be prepared by reacting a mixture of the appropriate orthanilamide derivative with the heterocyclic acid halide which, for practical purposes, can be the acid chloride. The acid chloride can be preformed and employed in the reaction or it can be prepared in situ by the addition of phosphorus oxychloride to a mixture of the orthanilamide and the heterocylclic carboxylic acid. When the acid chloride is preformed, the reaction advantageously is conducted in the presence of an inert solvent such as dioxane, tetrahydrofuran, dimethylformamide, and the like and is facilitated by heating up to the reflux temperature of the reaction mixture. When the heterocyclic acid chloride is formed in situ, the phosphorus oxychloride serves not only to form the acid chloride but as solvent as well.

A conventional method for preparing the 3,4-dihydrobenzothiadiazine of structure II above comprises reacting a mixture of the appropriate orthanilamide derivative with the heterocylic aldehyde, generally in the presence of a mineral acid. In those instances where a substituent is attached to either the heterocyclic moiety or the orthanilamide moiety that would be removed under acid conditions the reaction can take place in the presence of base such as an alkali metal hydroxide or the reaction time in the presence of a mineral acid can be closely followed to determine the point at which cyclization is effected. When acid labile groups are present the reaction generally is conducted at ambient temperature in the presence of mineral acid. When an alkali metal hydroxide is employed or when no acid labile groups are present the reaction mixture can be heated up to reflux conditions. It is well known that the 3,4-dihydro compounds (II) can be prepared from the hydro compounds (I) by reduction employing hydrogenation in the presence of ruthenium or by treatment with an alkali metal borohydride or an equivalent reducing agent capable of reducing the double bond. Various methods of reducing the double bond have been described in the literature and any one of these materials can be employed in converting the products of structure I to the products of structure II.

Pharmacologically acceptable salts generally are the alkali metal salts which may be prepared by conventional methods, for example by treatment with an alkali metal hydroxide, e.g. sodium or potassium hydroxide, in a solvent such as a lower alkanol or in water and evaporating the solvent or by reacting the free compound, for example, in an ether, e.g. p-dioxane or di-ethyleneglycol dimethyl ether solution with an alkali metal hydride or amide and removing the solvent. Mono- or poly-salts may be obtained.

The novel products of this invention are effective inhibitors of xanthine oxidase, in decreasing the concentration of uric acid in the blood and urine, and in increasing the excretion of hypoxanthine and xanthine. The products are therefore useful in the treatment and management of gout preferably by oral administration of from about 100 to 800 mg. per day in divided doses as prescribed by the physician.

The following methods were employed to prepare the products of Table I.

Method A

A mixture of the orthanilamide derivative (0.02 mole) and heterocyclic acid chloride (0.022 mole) in 75 ml. of dioxane or other inert organic solvent is heated under reflux conditions for about 24 hours. The mixture is chilled, the solid collected, washed with cold ether and dissolved in a mixture of 75 ml. of ethanol and 75 ml. of concentrated ammonium hydroxide. The solution is heated under reflux for three hours then concentrated to dryness in vacuo, the residue suspended in 100 ml. of water and the product precipitated upon acidification with hydrochloric acid. The product is purified by recrystallization from a mixture of dimethylformamide and water.

Method B

An intimate mixture of the orthanilamide derivative (0.01 mole) and heterocyclic carboxylic acid (0.01 mole) is heated with 20 ml. of phosphorus oxychloride for 15 minutes at 50° C. and for an additional 45 minutes on the steam bath. The solution is cooled and poured onto ice. The product is separated and then heated on the steam bath in a mixture of 50 ml. of ethanol and 50 ml. of concentrated ammonium hydroxide for 2 hours. After concentration in vacuo, the residue is treated with 50 ml. of water and the product separated by acidification with hydrochloric acid.

The products of Table I were prepared by the procedure of Method A or Method B as indicated in the table employing the orthanilamide and the heterocyclic carboxylic acid or acid halide having the substituents designated in the table. The substituents X, R, $R^1$ and $R^2$ of the starting materials appear unchanged in the end product, I.

Method C

A solution of the appropriate orthanilamide derivative (0.01 mole) and heterocyclic aldehyde (0.011 mole) in 60 ml. of water, 2 ml. of ethanol and 1.5 ml. of concentrated hydrochloric acid is heated under reflux for 2 hours. The hot mixture is filtered and the product purified by recrystallization from a mixture of dimethylformamide and water.

TABLE I $$X \longrightarrow \text{Ar} \longrightarrow NH_2 + R^2-COR^3 \longrightarrow X \longrightarrow \text{Ar} \longrightarrow N=R^2$$
$$RR^1NO_2S \qquad SO_2NH_2 \qquad\qquad RR^1NO_2S \qquad SO_2-NH$$
$$\text{I}$$

| Ex. No. | X | R | $R^1$ | $R^2$ | $R^3$ | m.p. °C | Meth of Syn. | Formula | Calculated C | H | N | Found C | H | N |
|---|---|---|---|---|---|---|---|---|---|---|---|---|---|---|
| 1 | Cl | $C_3H_7$ | $C_3H_7$ | pyrazinyl | Cl | 259–60 | A | $C_{17}H_{20}ClN_5O_4S_2$ | 44.59 | 4.40 | 15.29 | 44.86 | 4.36 | 15.06 |
| 2 | Cl | H | H | pyrazinyl | Cl | >360 | A | $C_{11}H_8ClN_5O_4S_2$ | 35.34 | 2.16 | 18.74 | 35.19 | 2.15 | 18.79 |
| 3 | Cl | H | H | 2-methylpyrazin-5-yl | Cl | >360 | B | $C_{12}H_{10}ClN_5O_4S_2$ | 37.16 | 2.60 | 18.06 | 37.59 | 2.71 | 17.83 |
| 4 | Cl | H | H | pyridazin-4-yl | OH | >360 | B | $C_{11}H_8ClN_6O_4S_2$ | 35.34 | 2.16 | 18.74 | 35.22 | 2.49 | 19.03 |
| 5 | $CF_3$ | H | H | pyridazin-4-yl | OH | >360 | B | $C_{12}H_8F_3N_5O_4S_2$ | 35.38 | 1.98 | 17.19 | 35.51 | 2.17 | 16.89 |
| 6 | $CH_3$ | H | H | 3-Cl-pyridazin-6-yl | OH | >350 | B | $C_{12}H_{10}ClN_5O_4S_2$ | 37.16 | 2.60 | 18.06 | 36.68 | 2.66 | 17.70 |
| 7 | Cl | H | H | 6-Cl-3-OH-pyridazin-4-yl | OH | 350 | B | $C_{11}H_7Cl_2N_5O_5S_2$ | 31.14 | 1.66 | 16.51 | 30.67 | 1.71 | 16.17 |
| 8 | Cl | H | H | pyrimidin-4-yl | OH | >360 | B | $C_{11}H_8ClN_5O_4S_2$ | 35.34 | 2.16 | 18.74 | 35.68 | 2.32 | 18.61 |
| 9 | $CF_3$ | H | H | pyrimidin-4-yl | OH | 325–27 | B | $C_{12}H_8F_3N_5O_4S_2$ | 35.38 | 1.98 | 17.19 | 35.54 | 2.02 | 17.24 |
| 10 | Cl | H | H | pyrimidin-2-yl | OH | >360 | B | $C_{11}H_8ClN_5O_4S_2$ | 35.34 | 2.16 | 18.74 | 35.54 | 2.13 | 18.54 |
| 11 | $CH_3$ | H | H | pyrimidin-4-yl | OH | >360 | B | $C_{12}H_{11}N_5O_4S_2$ | 40.78 | 3.14 | 19.82 | 40.65 | 3.27 | 19.45 |
| 12 | Cl | H | H | 2,6-$(OH)_2$-pyrimidin-4-yl | OH | >350 | A | $C_{11}H_8ClN_5O_6S_2$ | 32.56 | 1.99 | 17.26 | 33.18 | 1.92 | 17.29 |

EXAMPLE 13

6-Methyl-3-(pyridazin-3-yl)-7-sulfamoyl-1,2,4-benzothiadiazine-1,1-dioxide

A solution of 1.2 g. (0.003 mole) of 6-methyl-3(3'-chloro-6'-pyridazinyl)-7-sulfamoyl-1,2,4-benzothiadiazine-1,1-dioxide (prepared as described in Example 6) in 15 ml. of 10% sodium hydroxide solution and 5 ml. of ethanol is shaken in an atmosphere of hydrogen in a Parr apparatus in the presence of 200 mg. of 5% palladium on charcoal catalyst until the calculated uptake of hydrogen is consumed. The solution is filtered and the filtrate acidified. The product, when recrystallized from dimethylformamide-water, melts at 330°–335° C.

Analysis calculated for $C_{12}H_{11}N_5O_4S_2$: C, 40.78; H, 3.14; N, 19.82; Found: C, 40.74; H, 3.27; N, 19.49.

The general methods employed for preparing the 3,4-dihydrobenzothiadiazine compounds are described in the following Methods C-E.

Method D

A solution of the appropriate orthanilamide derivative (0.005 mole) and heterocyclic aldehyde (0.006 mole) in 22.5 ml. of ethanol and a solution of 90 mg. of sodium hydroxide in 2.5 ml. of water is heated under reflux for three hours, cooled and filtered. The product is precipitated from the filtrate upon acidification with hydrochloric acid and then purified by recrystallization from a mixture of dimethylformamide and water.

Method E

A solution of the appropriate orthanilamide derivative (0.01 mole) and heterocyclic aldehyde (0.02 mole) in 20 ml. of ethanol and 20 ml. of 6N hydrochloric acid is stirred at room temperature for one hour. The resulting solid is collected by filtration and purified by recrystallization from a mixture of dimethylformamide and water.

The substituents attached to the orthanilamide and heterocyclic aldehyde reactants as well as the end product, structure II, are identified in Table II along with the melting point and analysis for the end product obtained by the method of synthesis specified.

TABLE II $$X \longrightarrow \text{Ar} \longrightarrow NH_2 + R^2-CHO \longrightarrow X \longrightarrow \text{Ar} \longrightarrow N\overset{H}{\underset{}{\diagup}}R^2$$
$$RR^1NO_2S \qquad SO_2NHR^4 \qquad\qquad RR^1NO_2S \qquad SO_2 \diagdown N-R^4$$
$$\text{II}$$

| Ex. No. | X | R | $R^1$ | $R^2$ | $R^4$ | m.p. °C | Meth of Syn. | Formula | Calculated C | H | N | Found C | H | N |
|---|---|---|---|---|---|---|---|---|---|---|---|---|---|---|
| 14 | Cl | H | H | 2-methoxypyrazin-5-yl | H | 270–71 | C | $C_{12}H_{12}ClN_5O_5S_2$ | 35.51 | 2.98 | 17.26 | 35.88 | 3.03 | 17.16 |
| 15 | Cl | H | H | pyrazinyl | H | 228–29 | C | $C_{11}H_{10}ClN_5O_4S_2$ | 35.15 | 2.68 | 18.64 | 34.92 | 2.69 | 18.67 |
| 16 | Cl | H | H | 2-methoxypyrazin-5-yl | $CH_3$ | 233–35 | C | $C_{13}H_{14}ClN_5O_5S_2$ | 37.19 | 3.36 | 16.68 | 37.41 | 3.36 | 16.71 |
| 17 | Cl | H | H | 2-HO-pyrazin-5-yl | H | >360 | C | $C_{11}H_{10}ClN_5O_5S_2$ | 33.72 | 2.57 | 17.88 | 33.94 | 2.87 | 17.54 |
| 18 | Cl | H | H | 2-ethoxypyrazin-5-yl | H | 231–33 | D | $C_{13}H_{14}ClN_5O_5S_2$ | 37.19 | 3.36 | 16.68 | 37.55 | 3.42 | 16.62 |

TABLE II-continued

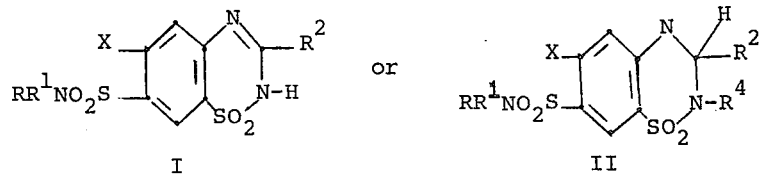

| Ex. No. | X | R | R¹ | R² | R⁴ | m.p. °C. | Meth of Syn. | Formula | Calculated C | H | N | Found C | H | N |
|---|---|---|---|---|---|---|---|---|---|---|---|---|---|---|
| 19 | Cl | H | H | 2-propoxypyrazin-5-yl | CH₃ | 234–37 | E | C₁₅H₁₈ClN₅O₅S₂ | 40.22 | 4.05 | 15.64 | 40.44 | 4.06 | 15.65 |
| 20 | Cl | H | H | 2-HO-pyrazin-5-yl | CH₃ | 274–76 | E | C₁₂H₁₂ClN₅O₅S₂ | 35.51 | 2.98 | 17.26 | 35.55 | 3.05 | 17.12 |
| 21 | Cl | H | H | 2-ethoxypyrazin-5-yl | CH₃ | 178–80 | E | C₁₄H₁₆ClN₅O₅S₂ | 38.75 | 3.72 | 16.14 | 39.09 | 3.89 | 16.21 |
| 22 | Cl | H | H | 2-methylpyrazin-5-yl | CH₃ | 247–48 | E | C₁₃H₁₄ClN₅O₄S₂ | 38.66 | 3.49 | 17.34 | 39.20 | 3.69 | 17.25 |
| 23 | Cl | H | H | 2-pentyloxypyrazin-5-yl | CH₃ | 215–17 | E | C₁₇H₂₂ClN₅O₅S₂ | 42.90 | 4.66 | 14.71 | 43.11 | 4.74 | 14.58 |

EXAMPLE 34

6-Chloro-2-methyl-3-(pyrimidin-4-yl)-7-sulfamoyl-3,4-dihydro-1,2,4-benzothiadiazine-1,1-dioxide This product is prepared by reacting 2-(N-methylsulfamoyl)-4-sulfamoyl-5-chloro aniline and pyrimidine aldehyde-4-diethylacetal according to the procedure of Method E.

What is claimed is:

1. A benzothiadiazine compound having the structure I or II and pharmacologically acceptable salts thereof wherein R is hydrogen or lower alkyl; $R^1$ is hydrogen or lower alkyl; $R^2$ is pyrimidinyl or a substituted pyrimidinyl derivative wherein the substituent is one or two similar or dissimilar groups selected from lower alkyl, lower alkoxy, hydroxy, chloro and bromo; $R^4$ is hydrogen or lower alkyl; and X is halo, lower alkyl and trifluoromethyl.

2. A benzothiadiazine product as claimed in claim 1 wherein $R^2$ is pyrimidinyl or substituted pyrimidinyl as defined in claim 1.

3. A product having structure I as claimed in claim 1 wherein R and $R^1$ are each hydrogen, X is chloro and $R^2$ is 4-pyrimidinyl.

4. A product having structure I as claimed in claim 1 wherein R and $R^1$ are each hydrogen, X is trifluoromethyl and $R^2$ is 4-pyrimidinyl.

5. A product having structure I as claimed in claim 1 wherein R and $R^1$ are each hydrogen, X is methyl and $R^2$ is 4-pyrimidinyl.

6. A product having structure I as claimed in claim 1 wherein R and $R^1$ are each hydrogen, X is chloro and $R^2$ is 2-pyrimidinyl.

7. A product having structure I as claimed in claim 1 wherein R and $R^1$ are each hydrogen, X is chloro and $R^2$ is 2,6-dihydroxypyrimidin-4-yl.

* * * * *